(12) United States Patent
Lin et al.

(10) Patent No.: US 7,276,071 B2
(45) Date of Patent: Oct. 2, 2007

(54) INTRAOCULAR LENS INJECTOR

(75) Inventors: James Lin, Poulsbo, WA (US); Andre J. Porter, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 888 days.

(21) Appl. No.: 10/751,364

(22) Filed: Jan. 5, 2004

(65) Prior Publication Data

US 2005/0149058 A1    Jul. 7, 2005

(51) Int. Cl.
*A61F 9/00* (2006.01)
*A61F 2/16* (2006.01)

(52) U.S. Cl. .................................... 606/107
(58) Field of Classification Search ........ 606/107–108; 623/6.11–6.12
See application file for complete search history.

(56) References Cited

U.S. PATENT DOCUMENTS

| | | | |
|---|---|---|---|
| 5,123,905 A | 6/1992 | Kelman | 606/107 |
| 5,190,552 A | 3/1993 | Kelman | 606/107 |
| 5,275,604 A * | 1/1994 | Rheinish et al. | 606/107 |
| 5,643,276 A | 7/1997 | Zaleski | 606/107 |
| 5,772,667 A | 6/1998 | Blake | 606/107 |
| 5,947,976 A * | 9/1999 | Van Noy et al. | 606/107 |
| 6,540,754 B2 * | 4/2003 | Brady | 606/107 |
| 7,033,366 B2 * | 4/2006 | Brady | 606/107 |

\* cited by examiner

*Primary Examiner*—Vy Q. Bui
(74) *Attorney, Agent, or Firm*—John H. Runnels; Bonnie J. Davis; James C. Carver

(57) ABSTRACT

A device and method for enhancing the surgical replacement of defective natural eye lenses with an intraocular lens. The device is an intraocular lens injector that prevents an intraocular lens from uncontrollably rotating or flipping as it is advanced towards a mammalian recipient's eye, while providing an ideal lens exit orientation to help reduce the occurrence of trauma. The lens injector comprises an insertion tube having a loading port and an ejection port, a plunger, a loading carriage, and a lens carrier. In one embodiment, the insertion tube allows for the controlled insertion of a lens by rolling one side of the lens onto itself as the lens is guided through the ejection port using a guide displaced in the insertion tube from a position near the loading port to the end of the ejection port. In an alternative embodiment, controlled insertion is achieved by rolling both sides of the lens at varying degrees so that one side eventually encircles the other side.

17 Claims, 5 Drawing Sheets

INTRAOCULAR LENS INJECTOR

This invention pertains to a surgical instrument, particularly an intraocular lens injector and method for inserting an intraocular foldable lens into a mammalian eye such as a human eye.

A "cataract" is a progressive clouding of an eye's natural lens. The "lens" is a part of the eye that helps focus light onto the retina, which in turn sends visual signals to the brain. To produce a sharp image on the retina, it is essential that the lens remains clear. Once the lens becomes cloudy, light rays are hindered from reaching the retina, which can result in blindness or diminished vision. Cataract surgery is often the most effective means for restoring vision loss from cataracts.

In most cases, cataract surgery involves removing a defective, natural eye lens and replacing it with an artificial intraocular lens ("IOL"). IOLs are clear, resiliently deformable (i.e., capable of being folded or rolled onto itself) lenses that focus light onto the retina. IOLs often include a lens body, referred to as an "optic," having an optically clear lens, and flexible fixation members, referred to as a "haptics," which extend from the optic to securely seat the lens in the visual axis of the eye. The optic is typically 5.5-6.0 mm in diameter. Once the cataract is removed, the IOL is folded and inserted into the eye through a small incision (approximately 2.4-3 mm long) in the cornea and into the capsular bag (the capsule is the natural membrane surrounding the cataract). A small corneal incision is necessary to minimize post-operative complications such as astigmatism, leaks, inadvertent ruptures, and slowed healing. See generally U.S. Pat. No. 5,190,552 and U.S. Pat. No. 5,643,276.

Current trends in cataract surgery are towards making smaller corneal incisions. The eye is then less likely to leak during the cataract removal process, the wound is more stable after surgery, the integrity of the cornea is stronger, and post-operative astigmatism is typically reduced. The incisions have typically been made larger than needed for cataract removal to accommodate either a folded lens or an injector with a larger diameter bore. More recently, some injectors have been created to fit through smaller incisions. To do so, many of the injectors employ a rotating plunger to advance the IOL. As the IOL advances, however, the lens often rotates axially through the bore of the injector such that the orientation upon ejection is difficult to control. A successful IOL insertion often depends on the surgeon's ability to control the orientation of the IOL as it is inserted into the eye. The orientation of the lens is critical for both the stability of the lens and the overall refraction of the eye. In some instances, the surgeon must extend the initial incision, so that the IOL orientation can be corrected. The axial rotation of the IOL also causes the haptics to rotate. As the haptics swing back-and-forth during injection, the posterior capsule can be cut. Loss of integrity of the capsule can cause multiple problems, including retinal tears or simply dropping the lens into the vitreous cavity.

U.S. Pat. No. 5,772,667 describes an intraocular lens injector for reducing the damage inflicted upon an intraocular lens during compression and insertion into an eye by rolling the lens into a tight cylindrical tube that can then be inserted into the eye.

U.S. Pat. No. 5,643,276 describes an apparatus and method for inserting a folded intraocular lens into an eye, comprising an insertion tube, an injector rod, and a rotation assembly for rotating the injector rod. The intraocular lens is oriented during insertion by rotating the injector rod as the intraocular lens is urged through the insertion tube to reduce the risk of eye damage as the intraocular lens enters the eye.

U.S. Pat. No. 5,190,552 describes an injector for injecting a temporarily folded intraocular lens in a controlled manner, by folding the lens into the injector so that the lens haptics protrude from a tube slot in the injector during insertion.

U.S. Pat. No. 5,123,905 describes an intraocular lens injector and method for controlled injection and unfolding of an intraocular lens in an eye comprising a head for partial insertion into a minimum size eye incision, and a device to push the folded lens through the head.

An unfilled need exists for a surgical instrument that enhances the ability to replace defective natural eye lenses with an IOL by eliminating or nearly eliminating the need to extend the corneal incision or to reorientate the IOL once it has been injected into the patient's eye.

We have discovered an inexpensive device and method for enhancing the surgical replacement of defective natural eye lenses with an intraocular lens. The novel invention is a standardized lens injector that allows for the implantation of various types, and prevents the lens from uncontrollably rotating or flipping as it is advanced towards the receiving eye, while providing an ideal lens exit orientation to help reduce the occurrence of eye trauma. The lens injector comprises an insertion tube having a loading port and an ejection port, a plunger, a loading carriage, and a lens carrier. In one embodiment, the insertion tube allows for the controlled insertion of a lens by rolling one side of the lens onto itself as the lens is guided through the ejection port, using a guide displaced in the insertion tube from a position near the loading port to the end of the ejection port. In an alternative embodiment, controlled insertion is achieved by rolling both sides of the lens to varying degrees so that one side eventually encircles the other side.

The general purpose of this invention is to provide a reliable, inexpensive means to replace damaged eye lenses with an IOL (e.g., Sensar and SI40 (Advance Medical Optics, Inc., Santa Ana, Calif.); MA60 and MA30 (Alcon, Fort Worth, Tex.); and CeeOn (Pfizer, Inc., Kalamazoo, Mich.)) by using a device capable of rolling the lens onto itself, or rolling both sides of the lens to varying degrees, such that one side eventually encircles the other side, and controllably guiding the lens into a patient's eye through a relatively small incision (preferably about 2.4-3.0 mm long, most preferably about 2.6 mm). The basic design of the device comprises an insertion tube having a loading port and an ejection port, a plunger, a loading carriage, and a lens carrier. In one embodiment, the insertion tube is a conically-shaped device comprising a receiving chamber and a guide chamber that converge at a location near the ejection port to form an ejection chamber having a guide ridge. In an alternative embodiment, the conically-shaped insertion tube comprises two receiving chambers that converge to form an ejection chamber having a guide ridge near the ejection port. Preferably, all components should be made of a biologically inert and sterilizable material, and should have a relatively high mechanical strength, such as polymethyl methacrylate, plastic, stainless steel, or titanium.

There are several advantages to the novel device. First, the potential for damaging the eye (e.g., iris, anterior chamber, posterior capsule, etc.) during lens implantation is substantially reduced. The need to reorientate the lens once it is positioned in the eye is nearly eliminated because the orientation of the lens as it is ejected into a recipient's eye is controlled. Second, post-operative astigmatism should be substantially reduced. The need to apply stitches is nearly eliminated because the lens can be implanted through a small incision capable of forming a water-tight, self-healing seal.

Figure 1:
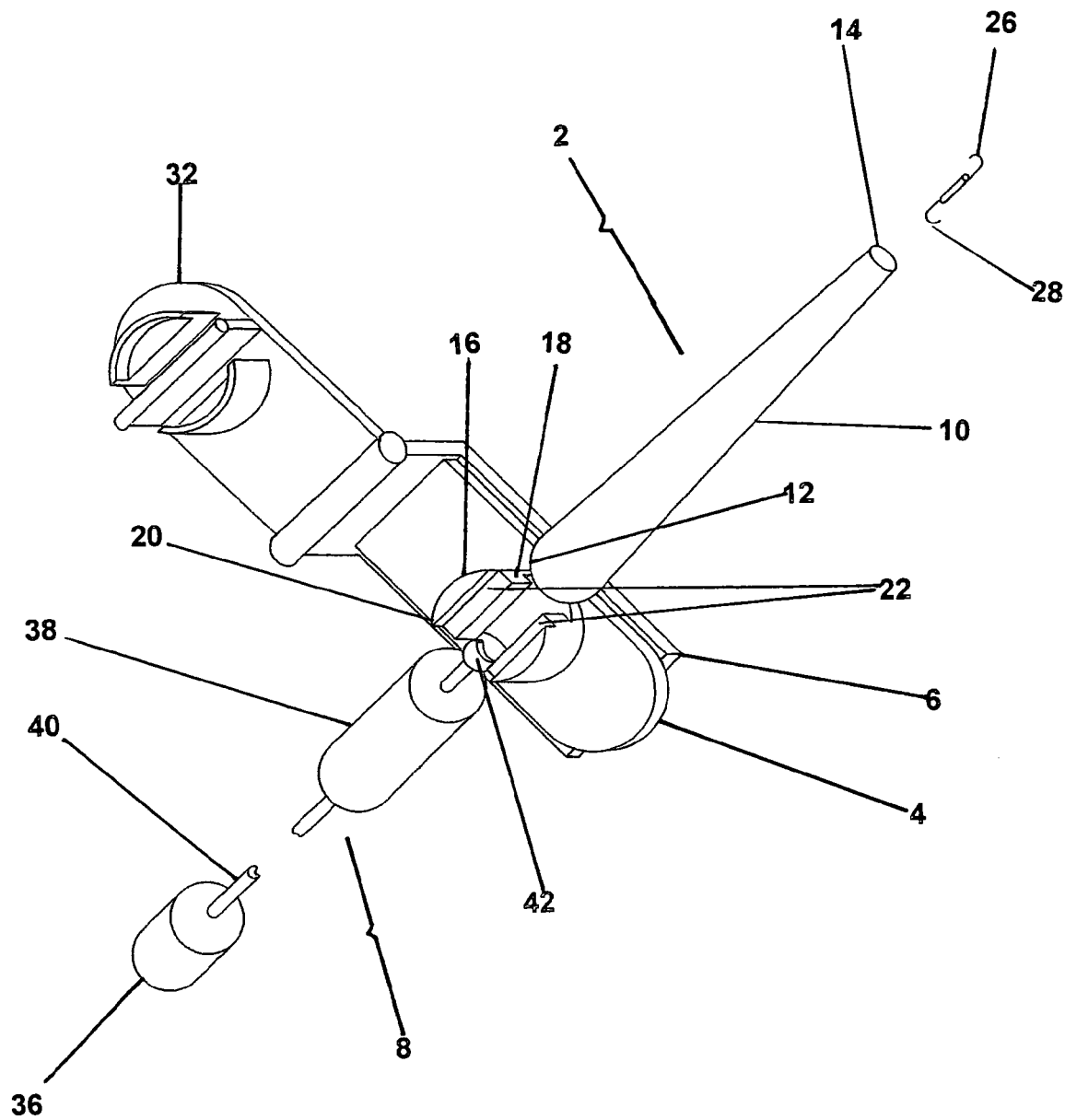
FIG. 1 illustrates a perspective view of one embodiment of the lens injector with the removable loading carriage cover removed.
Figure 2:
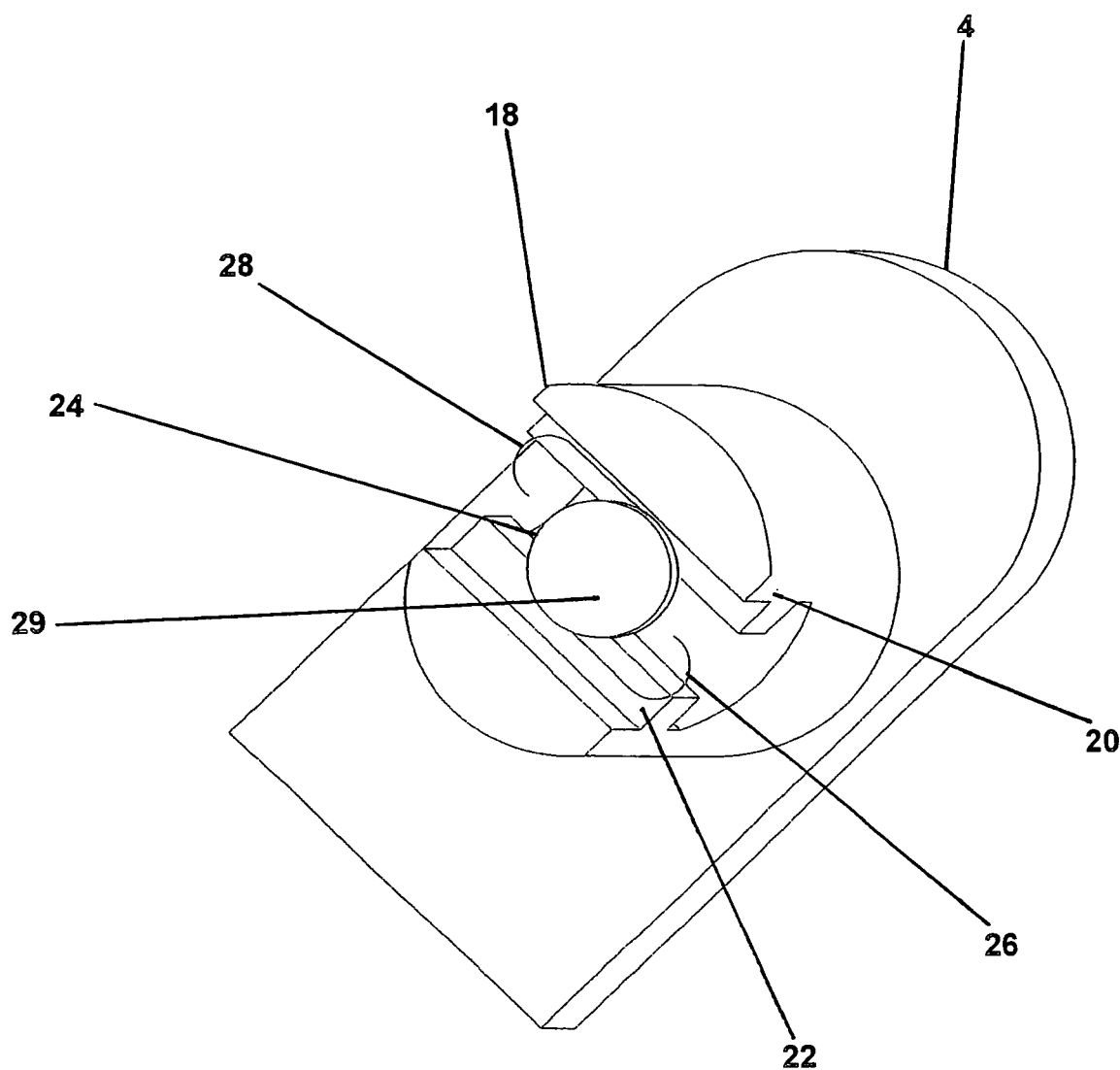
FIG. 2 illustrates a perspective view of one embodiment of the lens carrier with an IOL resting on the guides.

FIG. 1 illustrates one embodiment of a lens injector 2, in accordance with the present invention. In this embodiment, lens injector 2 comprises a removable lens carrier 4, a loading carriage 6 having a loading carriage cover 32, a plunger 8, and a conically-shaped insertion tube 10 having a loading port 12 and an ejection port 14. Removable lens carrier 4 comprises an encasement chamber 16 having a distal end 18 and a proximal end 20, a pair of guides 22, and a removable cover (not shown). See FIG. 2. To insert an IOL 24 (see IOL 24 in FIG. 2) having leading and trailing haptics (26 and 28, respectively) into lens carrier 4, IOL 24 is placed on top of guides 22 in a flat position with leading haptic 26 (see leading haptic 26 in FIG. 2) extending towards proximal end 20 and trailing haptic 28 (see trailing haptic 28 in FIG. 2) extending towards distal end 18. In this position, IOL 24 may be either stored for future use by securely fastening a removable cover (not shown) over encasement chamber 16, or chamber 16 may be loaded into insertion tube 10 for immediate use. Alternatively, pre-loaded lens carriers having IOLs with varying dimensions and shapes may be prepared to allow a surgeon to choose an appropriately-sized IOL, and immediately load and inject the IOL into the recipient's eye.

As illustrated in FIG. 1, plunger 8 comprises a handle 36, a plunger support 38, and a rod 40 having a tip 42. Plunger support 38 is sized and shaped to support rod 40, and to allow for the relatively smooth and easy advancement of rod 40 and tip 42 through insertion tube 10. The size and shape of rod 40 and tip 42 are adapted such that as handle 36 is pushed towards plunger support 38, tip 42 engages IOL 24 and smoothly propels it from lens carrier 4 through insertion tube 10 and into recipient's eye, without damaging IOL 24 (e.g., optic 29, leading haptic 26, or trailing haptic 28). See FIG. 2. Alternatively, plunger 8 may be adapted to allow for the relatively slow advancement of the IOL from lens carrier into insertion tube 10 by adding threads to at least a portion of rod 40 and plunger support 38 so that rod 40 may be slowly advanced by turning plunger support 38 until rod 40 engages a loaded IOL 24 and advances it into a loading port 12 (discussed more fully below).

Figure 3:
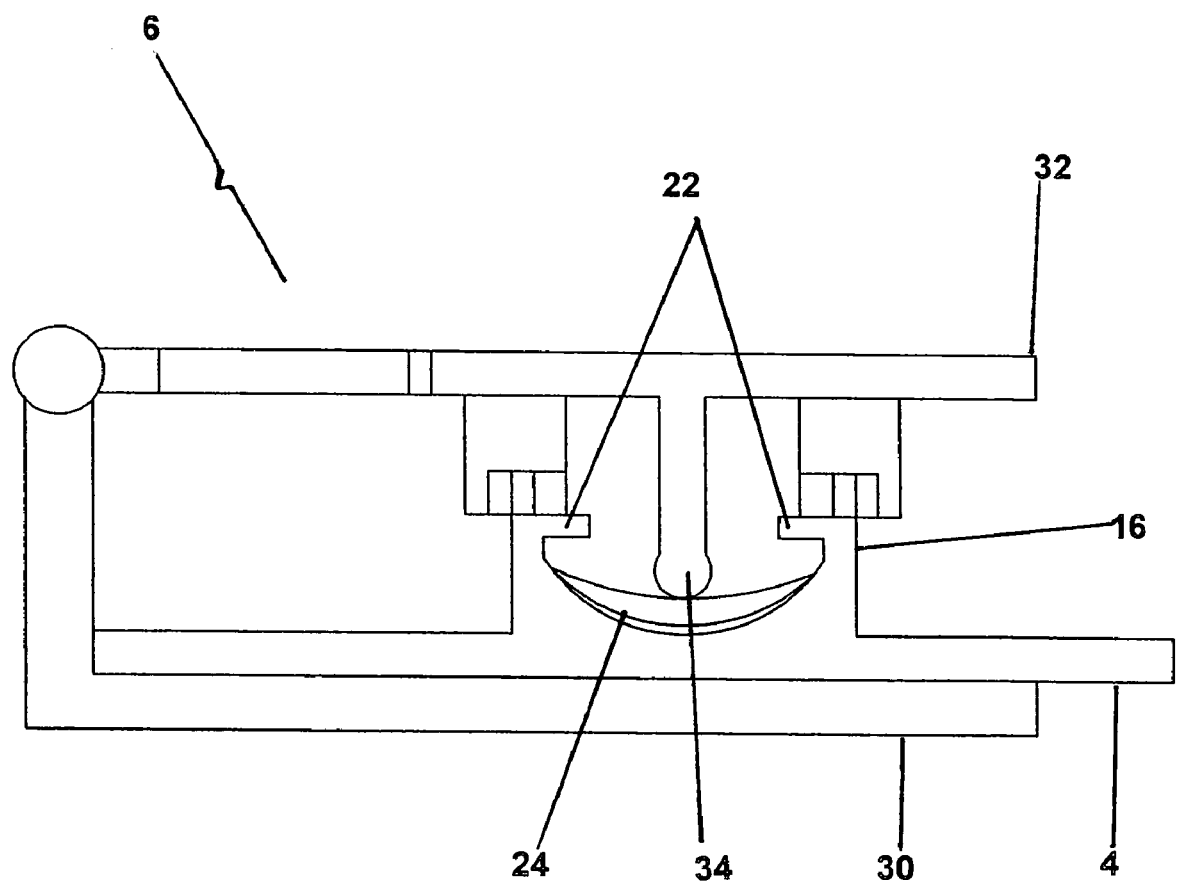
FIG. 3 illustrates a side plan view of one embodiment of the loading carriage and lens carrier combined with an IOL.

FIG. 3 illustrates a side plan view of one embodiment of the loading carriage 6 and lens carrier 4 combined. In this embodiment, loading carriage 6 comprises a docking platform 30 and a removable loading carriage cover 32 with a lens depressor 34. The size and shape of docking platform 30 compliment that of lens carrier 4 such that lens carrier 4 can be securely fastened onto docking platform 30 with proximal end 20 (see proximal end 20 in FIG. 1) of encasement chamber 16 positioned adjacent to loading port 12. See FIG. 1. Once lens carrier 4 and docking platform 30 have been combined, loading carriage cover 32 is placed over lens carrier 4 to allow for the securement and positioning of IOL 24 prior to its advancement into insertion tube 10. See FIG. 1. Lens depressor 34 and guides 22 are sized and shaped to allow for lens depressor 34 to press IOL 24 between guides 22 to align IOL 24, so that IOL 24 can be propelled from lens carrier 4 into insertion tube 10 (not shown).

Figure 4:
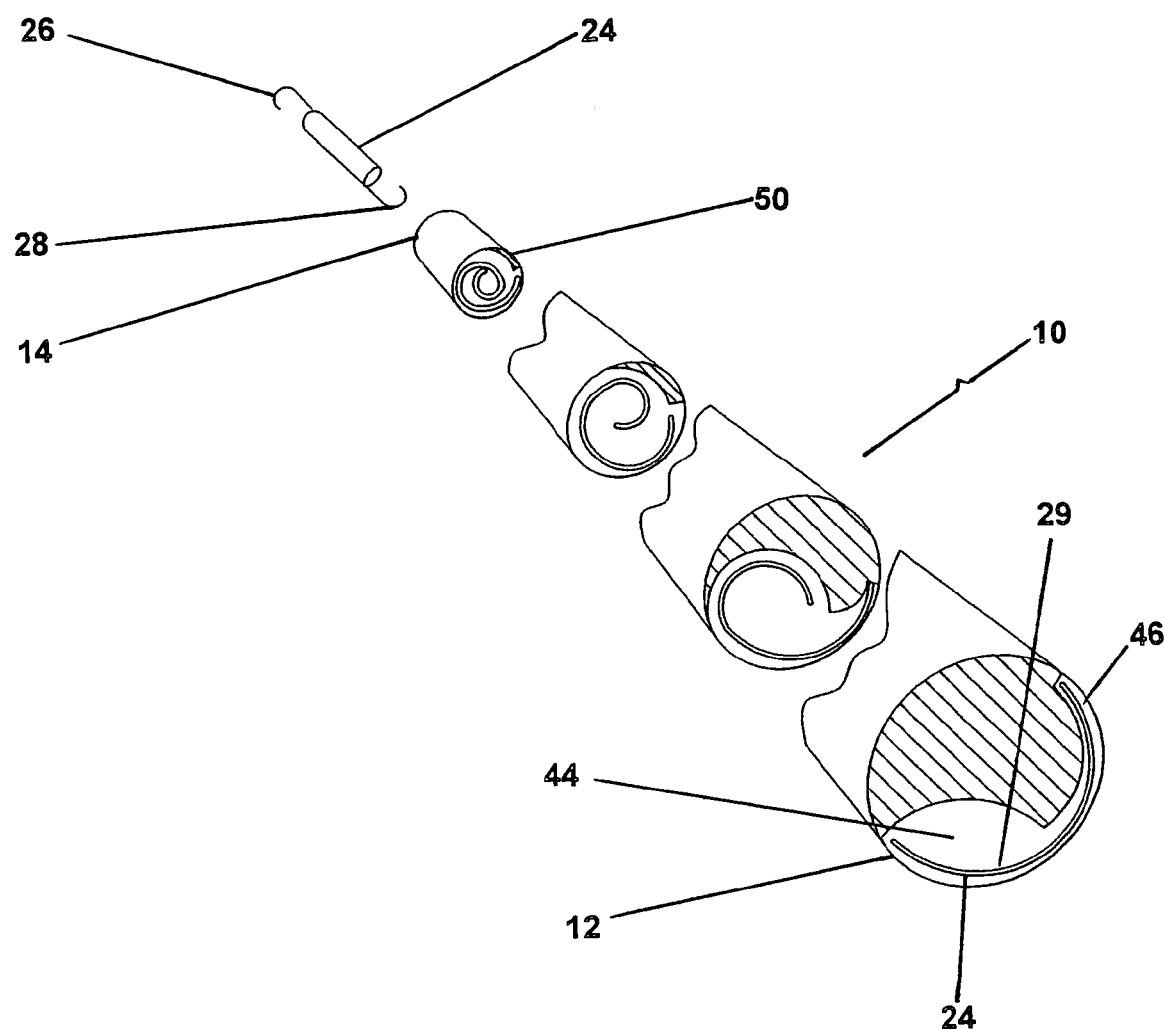
FIG. 4 illustrates a schematic view of one embodiment of the insertion tube for rolling one side of the lens onto itself as the lens is guided between the loading and ejection ports.

FIG. 4 illustrates a schematic view of one embodiment of insertion tube 10. In this embodiment, insertion tube 10 comprises a loading port 12 having a receiving chamber 44 and a guide chamber 46 adapted to communicate with one another, and to converge at a point near ejection port 14 to form an ejection port 14 having a guide ridge 50. Guide ridge 50 is adapted to prevent IOL 24 from rotating uncontrollably as it is advanced towards the recipient's eye, and to provide an ideal lens exit orientation in which the bowed posterior of the optic 29 is positioned away from the iris during insertion. This may be achieved by first positioning the IOL 24 on top of lens carrier 4 (not shown) such that optic 29 is centrally located with the bowed posterior of the optic 29 facing upwards, and the curved ends of each haptic (26 and 28) pointing in a counterclockwise direction, approximately 180° apart. See FIG. 2. The dimensions and shape of receiving chamber 44 compliment that of guide chamber 46 such that as IOL 24 is advanced towards ejection port 14, guide chamber 46 controllably propels a portion of IOL 24 towards receiving chamber 44, causing a portion of IOL 24 (located in receiving chamber 44) to roll over the bowed posterior of optic 29 without damaging IOL 24 (e.g., leading haptic 26, trailing haptic 28, optic 29). The diameter of ejection port 14 is sized such that IOL 24 is rolled relatively tight to a diameter of preferably about 2.6 mm before entering the eye.

Figure 5:
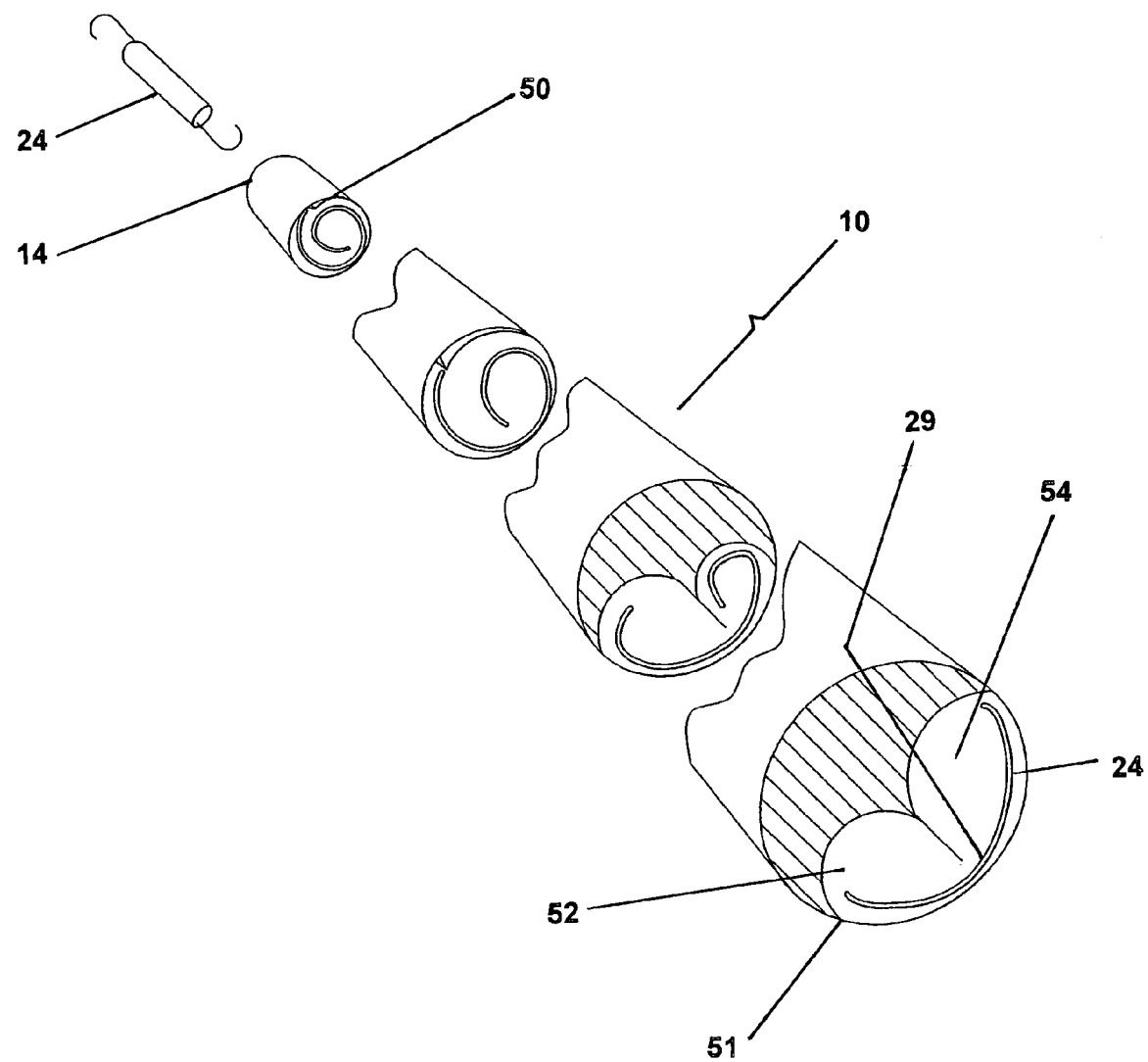
FIG. 5 illustrates a schematic view of one embodiment of the insertion tube for rolling both sides of the lens at varying degrees so that one side eventually encircles the other side as the lens is guided between the loading and ejection ports.

FIG. 5 illustrates a schematic view of another embodiment of insertion tube 10. In this embodiment, insertion tube 10 comprises a loading port 51 having a left receiving chamber 52 and right receiving chamber 54 that converge and form guide ridge 50 near ejection port 14. Guide ridge 50 is adapted to prevent IOL 24 from rotating uncontrollably as it is advanced towards the recipient's eye, and to provide an ideal lens exit orientation in which the optic 29 bows posteriorly away from the iris during insertion. The dimensions and shape of receiving chamber 52 compliment that of receiving chamber 54 such that as IOL 24 is advanced towards ejection port 14, both sides of IOL 24 begin to roll to varying degrees so that one side (the side of IOL 24 located in receiving chamber 52) eventually encircles the other side (the side of IOL 24 initially located in receiving chamber 54), without damaging IOL 24. The diameter of ejection port 14 is sized such that IOL 24 is rolled relatively tight to a diameter of preferably about 2.6 mm before entering the eye.

A preferred method of implanting an IOL 24 using lens injector 2 is to first bathe IOL 24 and all lens injection surfaces that may come into contact with IOL 24 in a viscous substance capable of lubricating IOL 24 to allow the IOL to glide through the injector, such as a viscoelastic gel (e.g., Healon, Healon 5, and Healon GV; Pfizer, Inc., New York, N.Y.). A viscoelastic gel also provides a liquid barrier that minimizes damage that may arise when the edges of optic 29 and haptics 26 and 28 make contact with the eye's capsular bag. IOL 24 is then placed on top of guides 22 in a relatively flat position, with leading haptic 26 extending towards proximal end 20, and trailing haptic extending towards distal end 18. Leading haptic 26 should be on the same side as guide chamber 46 when using insertion tube 10 as depicted in FIG. 4. Lens carrier 4 is then securely fastened onto loading carriage 6, and removable loading carriage cover 32 is placed over IOL 24 to align IOL 24 with injection tube 10. Handle 36 is then pushed towards loading port 12 to advance rod 40 towards IOL 24 until tip 42 engages IOL 24. When using insertion tube 10 as depicted in FIG. 4, rod 40 is slowly advanced to propel IOL 24 from lens carrier 4 into receiving chamber 44 and guide chamber 46. (When using insertion tube 10 as depicted in FIG. 5, rod 40 is slowly advanced to propel IOL 24 from lens carrier 4 into both receiving chambers 52 and 54.) Rod 40 and IOL 24 are then advanced through insertion tube 10 towards ejection port 14, which causes IOL 24 to become tightly rolled. Ejection port 14 is then placed in a small incision in the eye, and IOL 24 is advanced into the eye. Once optic 29 enters the eye, trailing haptic 28 may be easily positioned by spinning the lens into place with tip 42.

The complete disclosures of all references cited in this specification are hereby incorporated by reference. In the event of an otherwise irreconcilable conflict, however, the present specification shall control.

We claim:

1. A device for inserting an intraocular lens into a mammalian recipient's eye, comprising:
    (a) a removable lens carrier comprising an encasement chamber having a distal end and a proximal end, and a pair of guides for holding the intraocular lens;
    (b) an insertion tube comprising a loading port having first and second chambers adapted to communicate with each other, and to converge to form an ejection port having a guide ridge;
    (c) a loading carriage comprising a docking platform and a removable loading carriage cover having a lens depressor; wherein the size and shape of said docking platform are adapted to complement those of said removable lens carrier, such that said removable lens carrier may be securely fastened onto said docking platform with said proximal end of said encasement chamber positioned adjacent to said loading port; wherein said lens depressor and said guides are sized and shaped to allow for said lens depressor to press the intraocular lens between said guides to align the intraocular lens with said first and second chambers; and
    (d) a plunger comprising a handle, a plunger support, and a rod having a tip adapted to advance the intraocular lens towards said ejection port to allow for said guide ridge to controllably orient the intraocular lens and guide the lens into the eye.

2. A device as recited in claim 1, wherein said first chamber comprises a receiving chamber, and wherein said second chamber comprises a guide chamber; wherein when pressure is applied to said handle, the loaded intraocular lens is advanced towards said ejection port; wherein said guide chamber pushes the side of the intraocular lens contained therein towards said receiving chamber, causing the loaded intraocular lens to controllably roll onto itself in said receiving chamber as it traverses towards said ejection port; wherein the intraocular lens comprises a leading haptic and a trailing haptic; and wherein said guide ridge controllably orients the rolled intraocular lens and guides the lens into the eye with the leading haptic entering the eye first.

3. A device as recited in claim 1, wherein said first chamber comprises a first receiving chamber, and wherein said second chamber comprises a second receiving chamber; wherein when pressure is applied to said handle, the loaded intraocular lens is advanced towards said ejection port; wherein said receiving chambers roll both sides of the lens at varying degrees such that one side of the intraocular lens encircles the other side of the intraocular lens, causing the loaded intraocular lens to roll controllably onto itself as it reaches said ejection port; wherein the intraocular lens comprises a leading haptic and a trailing haptic; and wherein said guide ridge controllably orients the rolled intraocular lens and guides the lens into the eye with the leading haptic entering the eye first.

4. A device as recited in claim 1, wherein said insertion tube is conical.

5. A device as recited in claim 1, wherein said plunger support is sized and shaped to support said rod and to allow said tip to engage the intraocular lens and to advance the lens through said insertion tube.

6. A device as recited in claim 1, wherein said plunger support and said rod have threads sized and shaped to complement each other, such that said rod may be slowly advanced by turning said plunger support until said rod engages the loaded intraocular lens and pushes the intraocular lens into said loading port.

7. A device as recited in claim 1, wherein said ejection chamber has a diameter sized to roll the loaded intraocular lens to a diameter of about 2.6 mm as the lens exits through said ejection port.

8. A device as recited in claim 1, wherein said removable lens carrier additionally comprises a removable cover for storing a loaded intraocular lens in said removable loading carriage.

9. A device as recited in claim 1, additionally comprising a loaded intraocular lens pressed between said guides and aligned with said first chamber and said second chamber for insertion into the recipient's eye.

10. A method for inserting an intraocular lens into a mammalian recipient's eye from which the natural lens has been removed; said method comprising the steps of:
    (a) loading an intraocular lens having an optic and a leading haptic and a trailing haptic into a device as recited in claim 1;
    (b) rolling the intraocular lens tightly onto itself by pushing the intraocular lens through the insertion tube; and
    (c) placing the ejection port into a small incision in the eye and advancing the tightly rolled intraocular lens into the eye.

11. A method as recited in claim 10, wherein the insertion tube is conical.

12. A method as recited in claim 10, wherein the plunger support and the rod have threads sized and shaped to complement each other, such that the rod may be slowly advanced by turning the plunger support until the rod engages the loaded intraocular lens and advances it into the loading port.

13. A method as recited in claim 10, wherein the small incision is preferably about 2.4-3.0 mm long, most preferably about 2.6 mm.

14. A method as recited in claim 10, wherein the ejection chamber has a diameter sized to roll the loaded intraocular lens to a diameter of about 2.6 mm as it exits through the ejection port.

15. A method as recited in claim 10, wherein the removable lens carrier additionally comprises a removable cover for securing a loaded intraocular lens in the removable loading carriage when the loaded intraocular lens is not immediately injected into a mammalian recipient's eye.

16. A method as recited in claim 10, wherein the intraocular lens is loaded into the removable lens carrier by placing the intraocular lens on top of said guides in a flat position with the optic facing upward, the leading haptic extending towards the proximal end of the encasement chamber and trailing haptic extending towards the distal end of the encasement chamber.

17. A method as recited in claim 10, wherein the recipient is a human.

* * * * *